United States Patent
Nielsen et al.

(10) Patent No.: US 7,570,731 B2
(45) Date of Patent: Aug. 4, 2009

(54) IMAGING METHOD WITH BACK PROJECTION

(75) Inventors: Tim Nielsen, Hamburg (DE); Andy Ziegler, Hamburg (DE); Thomas Koehler, Norderstedt (DE); Roland Proksa, Hamburg (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 303 days.

(21) Appl. No.: 11/570,896

(22) PCT Filed: Jun. 24, 2005

(86) PCT No.: PCT/IB2005/052090

§ 371 (c)(1), (2), (4) Date: Dec. 19, 2006

(87) PCT Pub. No.: WO2006/000997

PCT Pub. Date: Jan. 5, 2006

(65) Prior Publication Data

US 2008/0273655 A1    Nov. 6, 2008

(30) Foreign Application Priority Data

Jun. 25, 2004    (EP) .................................. 04102956

(51) Int. Cl.
*A61B 6/03* (2006.01)

(52) U.S. Cl. .............................. 378/4; 378/19; 378/901; 382/131

(58) Field of Classification Search ...................... 378/4, 378/19, 901; 382/128–131
See application file for complete search history.

(56) References Cited

U.S. PATENT DOCUMENTS

| 6,002,738 A | 12/1999 | Cabral et al. |
| 6,529,575 B1 * | 3/2003 | Hsieh ............................. 378/4 |
| 6,654,440 B1 | 11/2003 | Hsieh |

OTHER PUBLICATIONS

Kohler et al., SNR-Weighted ART Applied to Transmission Tomography, Oct. 2003, 2003 IEEE Nuclear Science Symposium Record, vol. 4, p. 2739-2742.*

(Continued)

*Primary Examiner*—Edward J Glick
*Assistant Examiner*—John M Corbett

(57) ABSTRACT

The invention relates to an imaging method, especially a computerized tomography method, with which an object is penetrated by rays from different directions and measured values, which depend upon the intensity of the rays after penetrating the object, are acquired by a detector unit. From these measured values, an object image is reconstructed by means of back projection of measured-value-dependent back projection values. Therein, the object image is divided into overlapping, quasi-spherically symmetric image segments, each being defined by an image value and a quasi-spherically symmetric base function. Furthermore, during the back projection, the back projection values are added in proportions to the image values, wherein the proportion of a back projection value, which is added during the back projection to an image value, is dependent on a proportionality factor, which is equal to the average value of the line integrals of the base function belonging to the respective image value along those rays that have generated the measured value, on which the respective back projection value is dependent.

15 Claims, 8 Drawing Sheets

OTHER PUBLICATIONS

Figure 1:
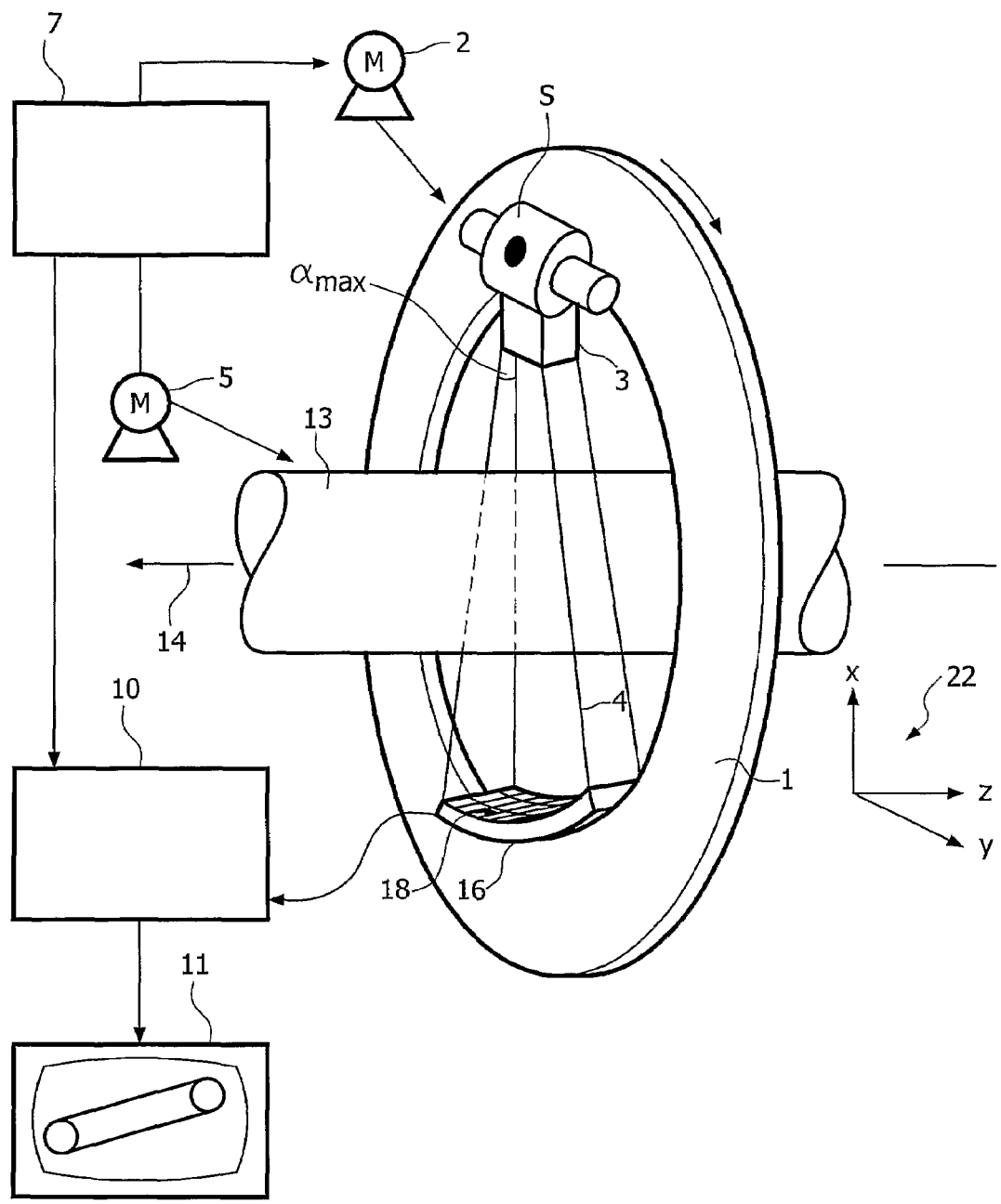

Matej et al., Practical Considerations for 3-D Image Reconstruction Using Spherically Symmetric Volume Elements, 1996, IEEE Transactions on Medical Imaging, vol. 15, No. 1, pp. 68-78.*

Lewitt, Alternatives to voxels for image representation in iterative reconstruction algorithms, 1992, Physics in Medicine and Biology, vol. 37, No. 3, pp. 705-716.*

Mueller, K., et al.; A Fast and Accurate Projection Algorithm for 3D Cone-Beam Reconstruction with the Algebraic Reconstruction Technique (ART); 1998; SPIE Medical Imaging Conference; pp. 1-9.

Mueller, K., et al., Rapid 3-D Cone-Beam Reconstruction with the Simultaneous Algebraic Reconstruction Technique (SART) Using 2-D Texture Mapping Hardware; 2000; IEEE Trans. on Medical Imaging; 19(12)1227-1237.

Mueller, K., et al.; Anti-Aliased Three-Dimensional Cone-Beam Reconstruction of Low-Contrast Objects with Algebraic Methods; 1999; IEEE Trans. on Medical Imaging; 18(6)519-537.

* cited by examiner

IMAGING METHOD WITH BACK PROJECTION

The invention relates to an imaging method, in particular a computerized tomography method, in which an object is penetrated by rays from different directions and with which measured values, which depend on the intensity of the rays after penetrating the object, are acquired with a detector unit. With the imaging method, measured value-dependent back projection values are back projected for the reconstruction of an object image, wherein the object image is divided into spherically symmetric, overlapping image segments (blobs). Moreover, the invention relates to a computer tomograph for executing the method as well as a computer program for operating the computer tomograph.

With an imaging method of the type mentioned above, back projection values, which are, for example, equal to the measured values, are back projected along a ray which, starting from the radiation source, centrally strikes the respective detector element. This type of back projection is disadvantageous, if the rays emanating from the radiation source diverge, since the spherically symmetric image segments, depending upon their distance from the radiation source, are penetrated differently by the rays during the back projection. An image segment that is relatively close to the radiation source is penetrated by more rays than an image segment that is at a greater distance from the radiation source. This leads to problems, since for the reconstruction of a good-quality image segment this image segment must be penetrated by a determinable minimum number of rays during the back projection. If this is not the case, then this is generally called "low scanning" of the image segment and aliasing-artifacts become visible in the object image.

Image segments, which are relatively remote from the radiation source, are frequently penetrated by very few rays during the back projection, so that aliasing-artifacts occur in the object image. A possibility of suppressing these aliasing-artifacts is to increase the size of the spherically symmetric image segments, so that even the image segments relatively remote from the radiation source are penetrated by a sufficient number of rays during the back projection. However, this considerably reduces the resolution of the object image.

It is therefore an object of the present invention to provide an imaging method of the type mentioned in the opening paragraph with which, even with divergent rays, object images with high resolution and reduced noise are reconstructed by aliasing artifacts and therewith, object images with an improved image quality in comparison to the state of the art.

This object is achieved according to the invention by an imaging method, particularly by a computerized tomography method, comprising:

Reconstruction of an object image by back projection of back projection values that depend on measured values, wherein the object image is divided into overlapping, quasi-spherically symmetric image segments, each one of which is defined by an image value and a quasi-spherically symmetric base function, wherein the back projection values are added in proportions to the image values during the back projection.

The term "quasi-spherically symmetric image segments" comprises both spherically symmetric image segments and image segments that can be brought into a spherically symmetric form by a linear coordinate transformation, for example, by a modification of an axis scaling. Similarly holds for the term "quasi-spherically symmetric base function".

With the imaging method according to the invention, back projection values that are dependent on the measured values are back projected, for example, a back projection value can be proportional or equal to a measured value. During the back projection a proportion of a back projection value is added to an image value, while this proportion is dependent on the average value of the line integrals of the base function belonging to the respective image value along those rays that have generated the measured value on which the respective back projection value is dependent. In contrast, with the above-mentioned known method, this proportion depends upon the line integral of the base function belonging to the respective image value along the ray which, starting from the respective radiation source, strikes the respective detector element centrally, without an average value being formed over several line integrals. This means that according to the invention back projection is not effected along a ray, as with the known method which, starting from the radiation source, strikes the respective detector element centrally, but back projection is effected along a beam, wherein this beam comprises all rays that strike the respective detector element from the radiation source. As a result, with the back projection, each spherically symmetric image segment is penetrated by a larger number of rays in comparison to the state of the art, so that the aliasing artifacts are reduced.

With a back projection, an inverse measuring process is simulated. With the measuring process itself, the intensity of the beam is detected, whose rays strike the respective detector element. With the known back projection method, the measured values are then back projected along a ray that strikes the respective detector element centrally starting from the radiation source. As a result of this, the inverse measuring process is simulated only insufficiently, since, as mentioned above, the detector element does not detect individual rays but a beam during the measurement, which beam comprises all the rays that strike the detector element. With the back projection according to the invention, this beam is taken into consideration in that the inverse measuring process is simulated more realistically. This improved simulation of the inverse measuring process, together with the reduction of aliasing artifacts, leads to an improvement of the quality of the reconstructed object image.

The imaging method in accordance with an embodiment, has a proportional dependency between the proportion of a back projection value, which is added to an image value during the back projection and the proportionality factor. This leads to a further improvement of the image quality.

In an embodiment, an imaging method is described, which determines the proportionality factor with a low cost of computation.

In the imaging method according to the invention and in accordance with an embodiment, the object image is reconstructed with an iterative method, which leads to a further improvement of the image quality.

In another embodiment, a computer tomograph is provided for executing the method according to the invention as described herein.

In another embodiment, a computer of a computer tomograph executes a computer program comprising instructions stored on computer memory of the computer and when executed on the computer, cause the computer to perform the method as described herein.

Figure 2:
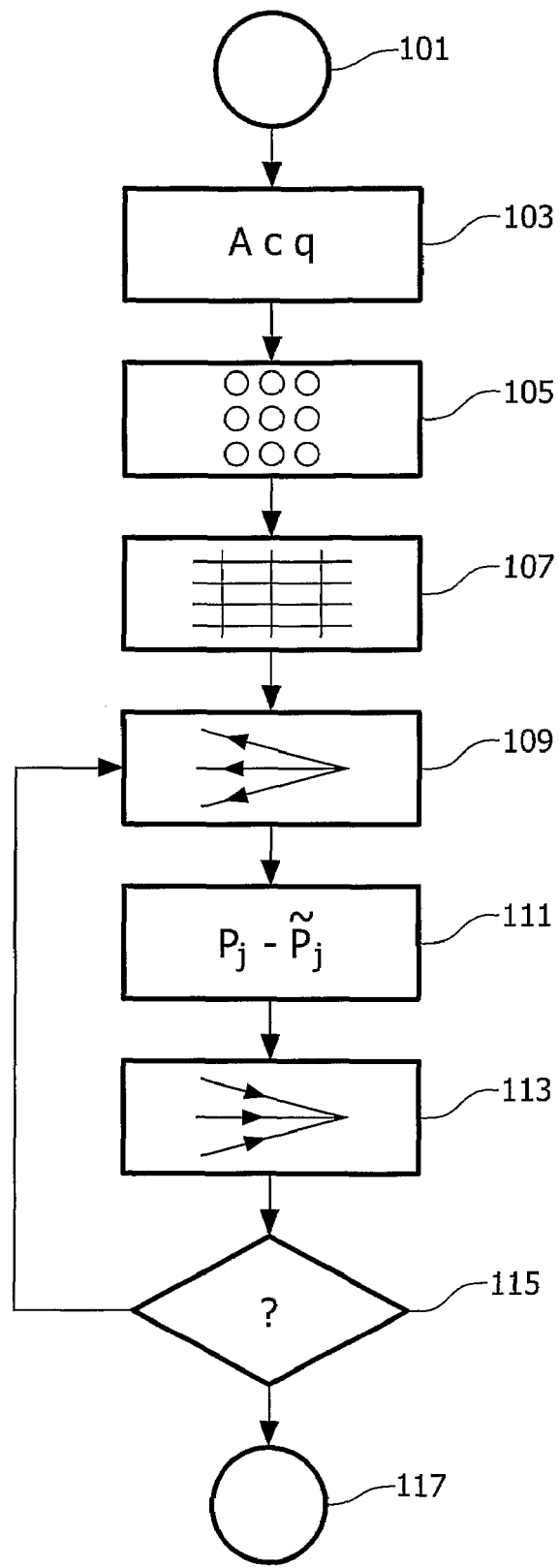
Figure 3:
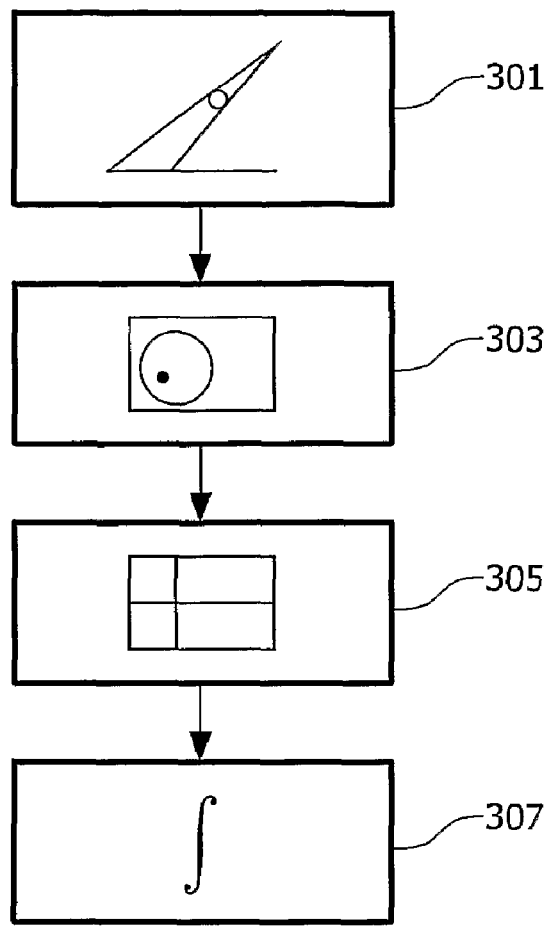
Figure 4:
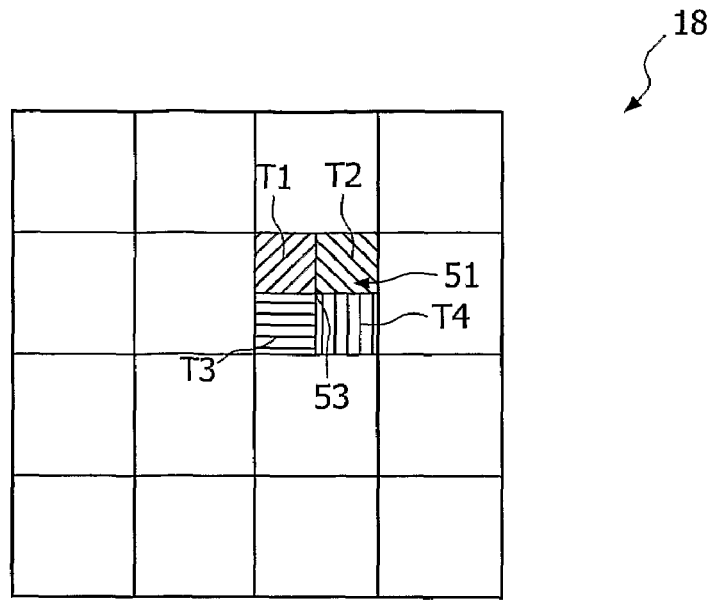
Figure 5:
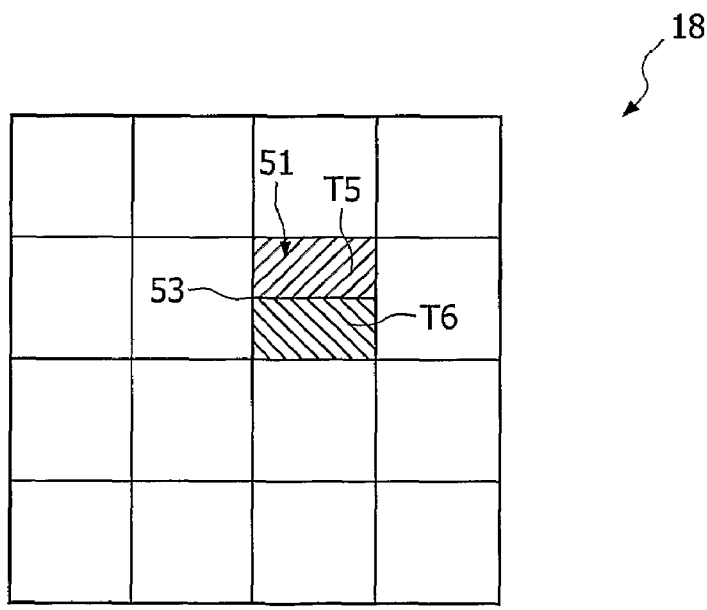
Figure 6:
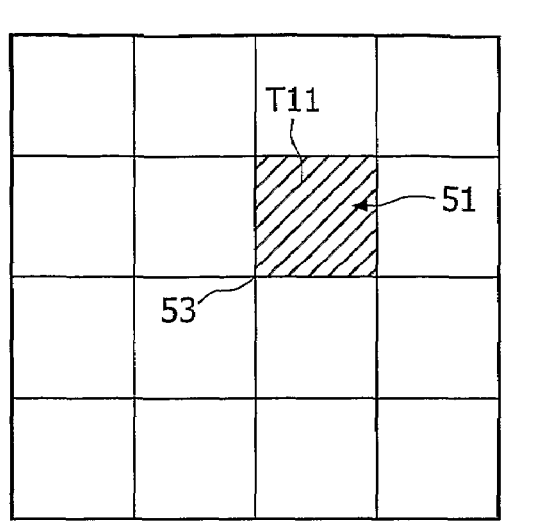
Figure 7:
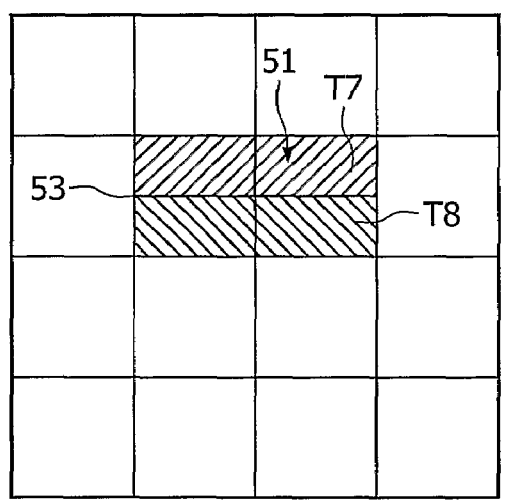
Figure 7:
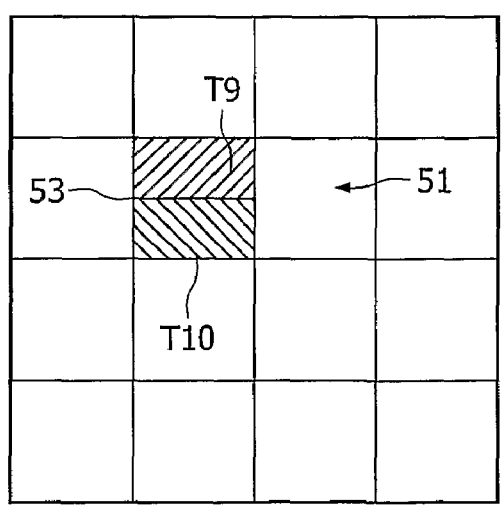
Figure 8:
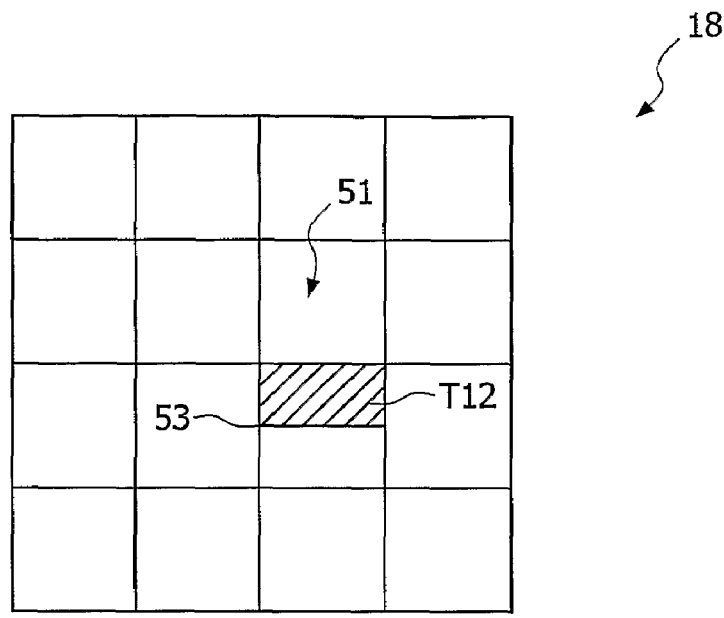
Figure 8:
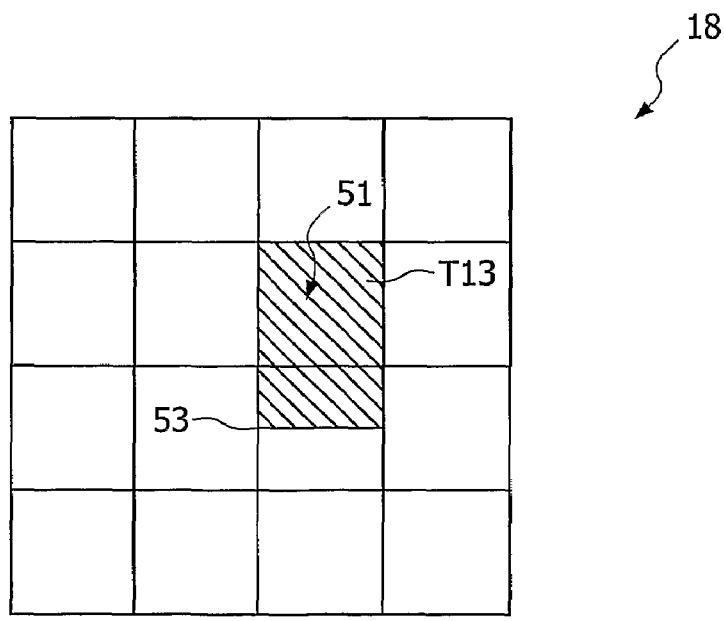
Figure 9:
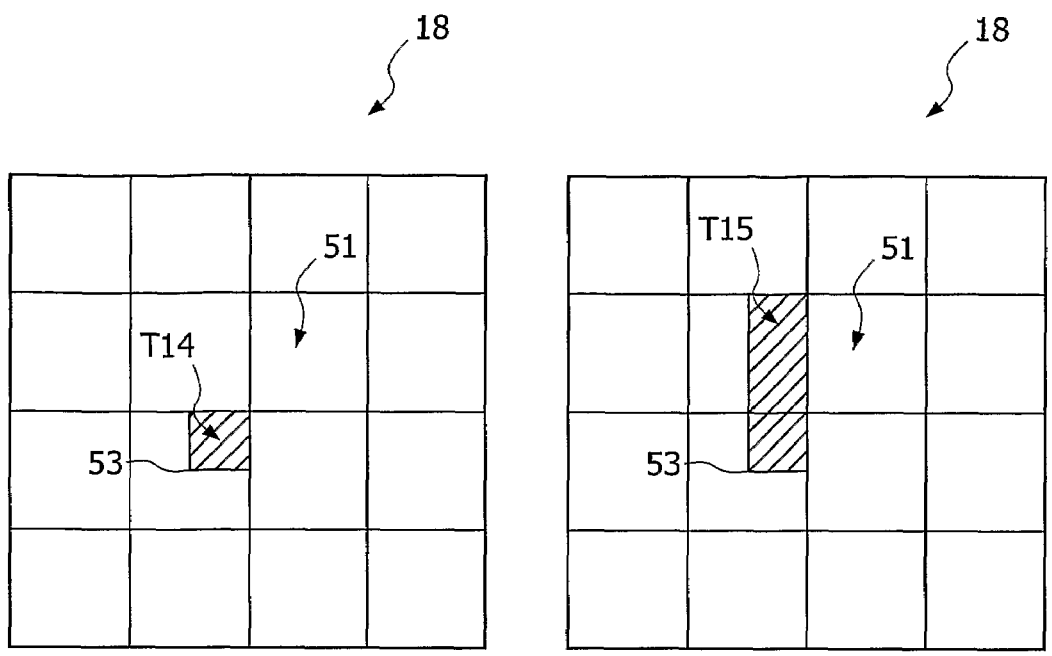
Figure 9:
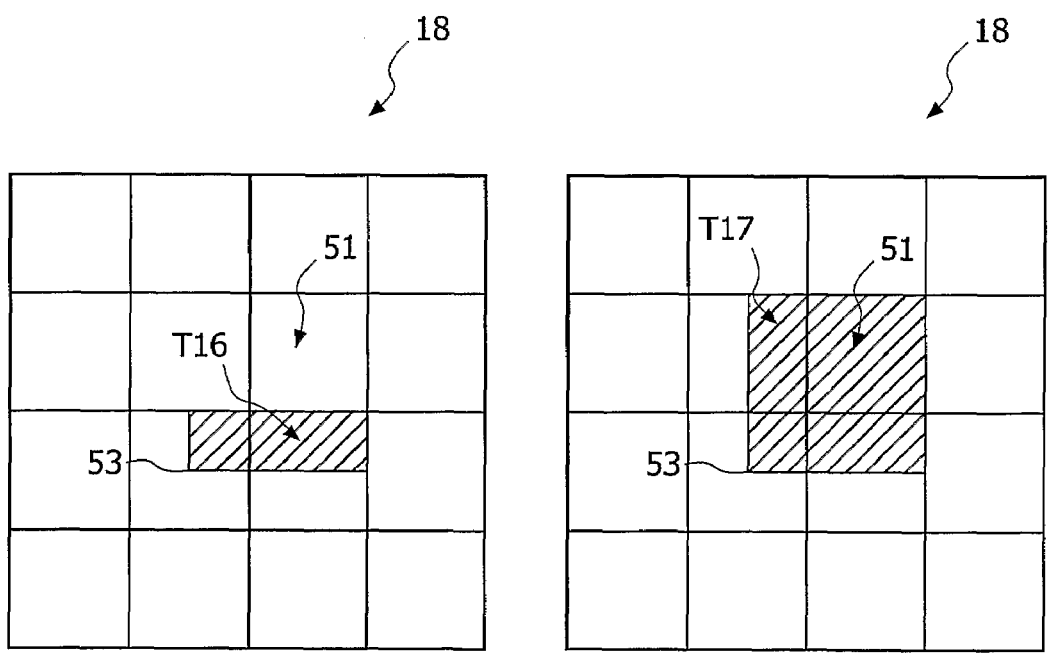
Figure 10:
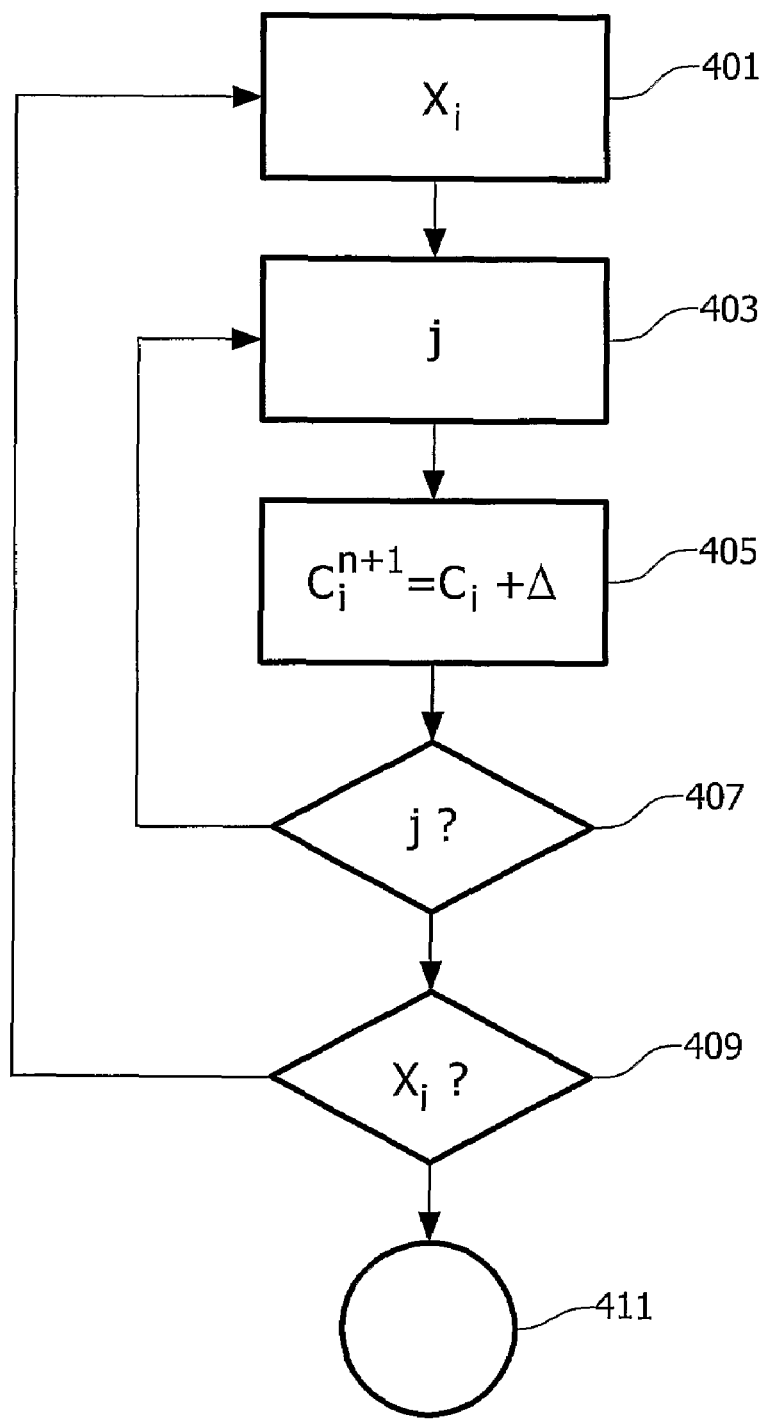

The invention is further explained hereinafter with reference to the drawings in which:

FIG. 1 shows a computer tomograph, with which the method according to the invention can be executed, FIG. 2 shows a flow chart of the method according to the invention, FIG. 3 shows a flow chart for generating sub-areas and average area values, with which a proportionality factor can be calculated at low computation cost, FIG. 4 to FIG. 9 show different sub-areas on a detector area and FIG. 10 shows a flow chart of a back projection.

The computer tomograph represented in FIG. 1 comprises a gantry 1, which can rotate around an axis of rotation 14 running parallel to the z-direction of the coordinate system 22 represented in FIG. 1. For this purpose, the gantry 1 is driven by a motor 2 with a preferably constant, but adjustable angular speed. A radiation source S, for example, an X-ray device is fastened to the gantry 1. This X-ray device is provided with a collimator arrangement 3, which extracts a cone-shaped beam 4 from the radiation generated by the radiation source S, that is, a beam that has a finite expansion different from zero, both in z-direction and in a direction perpendicular to it (that is, in a plane perpendicular to the axis of rotation).

The beam 4 penetrates a cylinder-shaped examination area 13 in which an object, for example, a patient on an examination table (neither is represented) or else a technical object can be located. After passing through the examination area 13 the beam 4 strikes a detector unit 16 with a detector area 18, which unit is fastened to the gantry unit 1, which detector area comprises a multiplicity of detector elements, which are arranged in rows and columns in a matrix in the form of a rectangle in this embodiment. The detector columns run parallel to the axis of rotation 14. The detector rows are located in planes perpendicular to the axis of rotation, in this embodiment on a circular arc around the radiation source S (focus-centered detector area). In other embodiments they may, however, be formed differently, for example, describe a circular arc around the axis of rotation 14 or be straight. Each detector element struck by the beam 4 provides a measured value for a ray from the beam 4 in each position of the radiation source.

The beam angle of the beam 4 referred to as $\alpha_{max}$ determines the diameter of the object cylinder, within which the object to be examined is located when the measuring values are acquired. The beam angle is then defined as the angle enclosed by a ray located in a plane perpendicular to the axis of rotation 14 on the edge of the beam 4, with a plane defined by the radiation source S and the axis of rotation 14. The examination area 13, or the object, or the examination table can be moved by means of a motor 5 parallel to the axis of rotation 14 or to the z-axis. Equivalently, however, also the gantry could be moved in this direction. If it is a technical object and not a patient, the object can be turned during an examination, while the radiation source S and the detector unit 16 remain still.

If the motors 2 and 5 run simultaneously, the radiation source S and the detector unit 16 describe a helix-shaped trajectory 17 relative to the examination area 13. If, on the other hand, the motor 5 for the feed in the direction of the axis of rotation 14 stands still and the motor 2 causes the gantry to rotate, there is a circular trajectory for the radiation source S and the detector unit 16 relative to the examination area 13. In the following example of embodiment only the helix-shaped trajectory is considered.

The measured values acquired by the detector unit 16 are applied to a reconstruction computer 10 (reconstruction unit), which is connected to the detector unit 16, for example, by a contactlessly operating data transmission (not represented). The reconstruction computer 10 reconstructs the absorption distribution in the examination area 13 and displays it, for example, on a monitor 11. The two motors 2 and 5, the reconstruction computer 10, the radiation source S and the transfer of the measured values from the detector unit 16 to the reconstruction computer 10 are controlled by a control unit 7.

The individual steps of an embodiment of the imaging method according to the invention are explained hereinafter with reference to the flow chart in FIG. 2.

After the initialization in step 101 the gantry rotates with an angular speed, which is constant in this embodiment. But it can also vary, for example, depending on the time or the position of the radiation source.

In step 103 the examination area or the examination table is moved parallel to the axis of rotation 14 and the radiation of the radiation source S is switched on, so that the detector unit 16 can detect the radiation from a multiplicity of angle positions and the radiation source S moves relative to the examination area 13 along the helix-shaped trajectory 17.

In step 105 an initial object image, divided into spherically symmetric, overlapping image segments (blobs) is pre-defined, each image segment having an image value and a spherically symmetric base function. The image segments are arranged in the object image at grid points of a three-dimensional, cartesian grid. Such a division of the object image can be represented by the following equation:

$$f(x) = \sum_i c_i b_i(x) \qquad (1)$$

Herein f(x) describes the object image, that is, if, for example, an absorption distribution of the object is to be reconstructed, f(x) represents the absorption value at the point x. Furthermore, $x_i$ are the grid points at which the image segments are arranged. Besides, $c_i$ is the image value and $b_i(x)$ is the spherically symmetric base function of the image segment arranged at the grid point $x_i$. The image values are initially equal to zero in this embodiment. The base functions $b_i(x)$ are all equal here, so that $b(x-x_i)$ could be substituted for $b_i(x)$ in equation (1).

As mentioned above, the image segments are arranged at grid points of a three-dimensional, Cartesian grid. Alternatively, the image segments may also be arranged at grid points of another type of grid, for example, at grid points of a hexagonal, cubic area-centered or cubic space-centered grid. Furthermore, the image segments may also be arranged at grid points of a two-dimensional grid, for example, if a two-dimensional object, like for example, a layer of a three-dimensional object, is to be reconstructed.

The base function $b_i(x)$ is spherically symmetric. Alternatively, it could also be arranged in a way that it can be brought into a spherically symmetric form by a linear transformation, for example, by an axial scaling.

In step 107 a table is provided, in which each combination of radiation source position, image segment and detector element is assigned one or more sub-areas of the detector area of the detector unit 16 and average area values assigned to these sub-areas.

The sub-areas, which are assigned to a combination of radiation source position, image segment and detector element, are determined in accordance with the steps represented in FIG. 3.

First, in step 301, the base function of the image segment is projected onto the detector area of the detector unit 16 along the rays emanating from the radiation source position. That is, for each ray emanating from the radiation source position, line integrals of the base function of the image segment are formed along the respective ray and the value of this line integral is put at the point of impact of the respective ray on the detector area.

Then, in step 303, the projection center of the base function of the image segment is determined, that is, the position of the projection of the center of the base function of the image segment on the detector area.

In step 305 the sub-areas are determined. The sub-areas are rectangular. They are selected in such a way that for each sub-area, a corner coincides with the projection center of the base function of the image segment determined in step 303 and that the diagonally opposite corner of the respective sub-area coincides with a corner of the detector element. This leads to the fact, that sub-areas are determined for a combination of radiation source position, image segment and detector element 1, 2 or 4, depending on where the projection center of the base function of the image segment is located relative to the detector element on the detector area. This is further explained hereinafter in connection with the FIGS. 4 to 9.

After the sub-areas have been determined for each combination of radiation source position, image segment and detector element, in step 307 for each sub-area, the average value of the base function projected in step 301 is calculated of the respective sub-area concerned, that is, the average value of the line integrals determined in step 301 is calculated, which line integrals are located on the sub-area concerned.

After one or more sub-areas and average area values have been determined for each combination of radiation source position, image segment and detector element and provided in a table, the object image is iteratively reconstructed in the following steps. One iteration step herein comprises the steps 109, 111 and 113.

In addition, in step 109 a forward projection is performed for each combination of radiation source position and detector element, which projection can be described by the following equation:

$$\tilde{p}_j = \sum_i w_{ji} c_i^n \qquad (2)$$

Herein, $\tilde{p}_j$ is a fictitious intermediate measured value obtained by forward projection. The index j herein features the respective combination of radiation source position and detector element or the beam that is determined by this combination. That is, for each combination of radiation source position and detector element, $\tilde{p}_j$ defines the intermediate measured value obtained by forward projection along the rays emanating from the respective radiation source position and striking the respective detector element. Moreover, $c_i^n$ defines the image value of the image segment arranged at the point $x_i$ after the n-th iteration of the iterative reconstruction method. Initially, the image values $c_i^0$ are set to zero. Alternatively, the image values $c_i^0$ can have other initial values. Furthermore, $w_{ji}$ describes a proportionality factor, which indicates, to what proportions the image values $c_i^n$ are added for generating the intermediate measured value $\tilde{p}_j$.

For determining the proportionality factor $w_{ji}$, the base function $b_i(x)$ provided at the point $x_i$ for the radiation source point of the $j^{th}$ combination of radiation source position and detector element is projected onto the detector area, as explained above in connection with step 301. Then the average value of this projection is calculated from the area of the detector element of the $j^{th}$ combination of radiation source position and detector element, that is, the line integrals of the base function $b_i(x)$ along the rays that strike the detector element of the $j^{th}$ combination of detector element and radiation source position, are averaged. The resulting average value is the proportionality factor $w_{ji}$.

The formation of the average values of line integrals is effected preferably by arithmetic averaging.

With forward projection, a fictitious intermediate measured value is determined for each measured value and thus for each combination of radiation source position and detector element, wherein the respective image values $c_i^n$ are first multiplied by the proportionality factor $w_{ji}$ and then added together.

The proportionality factors $w_{ji}$ in this embodiment are calculated with the help of the table provided in step 107.

The table contains one or more sub-areas and relevant average area values for each combination of radiation source position, image segment and detector element. For calculating the proportionality factor $w_{ji}$, the sub-areas and associated average area values, which are assigned to the $j^{th}$ combination of radiation source position and detector element and the image segment at the point $x_i$ are inferred from the table. Then the sub-areas inferred from the table are added together and/or subtracted so that they are equal to the area of the detector element of the $j^{th}$ combination of radiation source position and detector element. The average area values assigned to the sub-areas are then similarly added together and/or subtracted, while the result of the similar addition and/or subtraction is the respective proportionality factor. Similarly, addition and/or subtraction is explained with reference to the FIGS. 4 to 9.

How the sub-areas and thus the associated average area values are subtracted and/or added together, depends on the position determined in step 303 of the projection center of the base function $b_i(x)$ of the image segment at point $x_i$ relative to the detector element of the j-th combination of radiation source position and detector element.

This is represented hereinafter with reference to the sections of the detector area 18 represented in the FIGS. 4 to 9. In the FIGS. 7 to 9 the respective section of the detector area 18 is shown several times, in order to be able to represent overlapping sub-areas separately from each other.

If the projection center 53 of the base function $b_i(x)$ is located on the detector element 51 of the $j^{th}$ combination of radiation source position and detector element and not on the edge of the detector element 51 (FIG. 4), four sub-areas T1, T2, T3, T4 can be inferred from the table, which are added together, in order to obtain the area of the detector element 51. The proportionality factor $w_{ji}$ would then be equal to the total of the average area values assigned to the sub-areas T1, T2, T3, T4.

If the projection center 53 of the base function $b_i(x)$ is located on the edge of the detector element 51 of the $j^{th}$ combination of radiation source position (FIG. 5), then two sub-areas T5 and T6 can be inferred from the table, which are to be added together, in order to obtain the area of the detector element 51. The proportionality factor $w_{ji}$ would then be equal to the total of the average area values assigned to the sub-areas T5 and T6.

If the projection center 53 of the base function $b_i(x)$ of the i-th image value segment is located in a corner of the detector element 51 of the $j^{th}$ combination of radiation source position and detector element (FIG. 6), then a sub-area T11 can be inferred from the table. In this case the average area value assigned to this sub-area T11 is equal to the proportionality factor $w_{ji}$.

If the projection center 53 of the base function $b_i(x)$ is not located on the detector element 51 of the $j^{th}$ combination of radiation source position and detector element, but in the same detector row or column and not on an edge of a detector element (FIG. 7), then four sub-areas T7, T8, T9, T10 can be inferred from the table. The area of the detector element 51 results from subtracting the two smaller sub-areas T9, T10 from the total of the two larger sub-areas T7, T8 (T7+T8−T9−T10). Correspondingly, the average area values assigned to these sub-areas would then have to be added together or subtracted, in order to obtain the proportionality factor $w_{ji}$.

If the projection center 53 of the base function $b_i(x)$ is not located on the detector element 51 of the $j^{th}$ combination of radiation source position and detector element, but in the same detector row or column and on an edge of a detector element (FIG. 8), then two sub-areas T12, T13 can be inferred from the table. The area of the detector element 51 results from subtracting the sub-area T12 from the sub-area T13. For calculating the proportionality factor $w_{ji}$ the average area value, which is assigned to the sub-area T12, would in this case have to be subtracted from the average area value that is assigned to the sub-area T13.

If none of the aforementioned cases described in connection with the FIGS. 4 to 8 is present, then four sub-areas T14, T15, T16, T17 can be inferred from the table (FIG. 9). The largest sub-area T17, for which the corner that is diagonally across from the projection center 53 is farthest from the projection center 53, and the smallest sub-area T14, for which the corner that is diagonally across from the projection center 53 is closest to the projection center 53, are added together and the remaining two sub-areas T15, T16 are subtracted from the resulting total in order to obtain the area of the detector element 51. For calculating the proportionality factor $w_{ji}$ the average area values, which are assigned to the sub-areas T14 and T17 would then have to be added together and the average area values which are assigned to the sub-areas T15 and T16 would have to be subtracted from the resulting total.

In practice, the projection center 53 of the respective base function will mostly not be located on the edge of a detector element. Therefore, as a rule, four sub-areas are used for the calculation of the proportionality factor.

After the forward projection, differences $p_j - \tilde{p}_j$ between the measured values $p_j$ and the fictitious intermediate measured values $\tilde{p}_j$ are formed as back projection values in step 111.

In step 113 the differences, that is, the back projection values are back projected for each $j^{th}$ combination of radiation source position and detector element and for each image segment arranged in the point $x_i$, in accordance with the following equation:

$$c_i^{n+1} = c_i^n + \lambda_n \frac{p_j - \tilde{p}_j}{\sum_i w_{ji}^2} w_{ji} \quad (3)$$

Herein, $\lambda_n$ is a proportionality factor of the $n^{th}$ iteration. The proportionality factor $\lambda_n$ determines, how strongly the image values $c_i^n$ change from one iteration step to the next and can optionally be predefined. The proportionality factor $\lambda_n$ equals 1.

The back projection, in accordance with equation (3), can be executed in accordance with the flow chart represented in FIG. 10.

Initially, in step 401 a point xi is determined in which no image value $c_i^n$ has yet been changed in this iteration step.

Then, in step 403, a combination of radiation source position and detector element is predefined, which combination has not yet been used in this iteration step for the image value $c_n^i$. This combination is again referred to by the index j.

In step 405 the difference $p_j - \tilde{p}_j$ defined by the combination of radiation source position and detector element selected in step 403, which difference represents the back projection value, is multiplied by the proportionality factor $w_{ji}$ and divided by a scale factor. In this example of embodiment the scale factor is equal to the total of the squares of those proportionality factors $w_{ji}$ that are assigned to the combination of radiation source position and detector element selected in step 403. If the proportionality factor $\lambda_n$ in other examples of embodiment does not equal 1, then the difference $p_j - \tilde{p}_j$ is additionally multiplied by $\lambda_n$. The scaled difference multiplied by the proportionality factor and if necessary by $\lambda_n$, is added to the image value $c_i^n$ at the point $x_i$.

In step 407 checks are made whether all combinations of radiation source position and detector element, which led to a measured value with the acquisition in step 103, have been considered for the image value $c_i^n$ in this iteration step. If this is not the case, then step 403 is proceeded with.

Otherwise, in step 409 checks are made whether at all points $x_i$ of the object image, the image values $c_i^n$ have been changed in this iteration step. If this is not the case, then step 401 is proceeded with.

Otherwise the back projection of this iteration ends in step 411.

In step 115 checks are made whether an abort criterion is satisfied. This abort criterion may be, for example, achieving a predetermined number of runs of the iterative method. Moreover, the abort criterion could be that the total of the square differences of the fictitious intermediate values and of the measured values $$\sum_j (p_j - \tilde{p}_j)^2$$

falls below a predefined threshold value. If this abort criterion is not satisfied, then step 109 is proceeded with. Otherwise the imaging method ends in step 117.

The imaging method according to the invention is not limited to iterative methods. The invention in fact comprises each imaging method that uses a back projection for the reconstruction of an object image, wherein when a back projection value depending on a measured value is to be back projected, the proportionality of the back projection value that is added to an image value is dependent on the average value of the line integrals of the base function belonging to the image value along those rays that have generated the measured value on which the respective back projection value is dependent. Therefore, the invention also comprises, for example, imaging methods, which use a filtered back projection, which methods take into account the proportion of a back projection value that is added to an image value, as described above.

Moreover, the imaging method according to the invention is not limited to the reconstruction of measured values, which were produced with a computer tomograph. For generating the measured values, each modality can be used that penetrates an object to be represented by rays in different directions and acquires measured values that depend on the intensity of the rays after penetrating the object. Therefore, the measured values can also be produced according to the invention with a C-Arc-System, a Positron Emission Tomograph (PET) or a Single Photon Emission Computerized Tomography (SPECT).

In the example of embodiment described, base functions are projected onto the detector area and sub-functions and average values are determined on this detector area. Alternatively, the same views could be valid in any optional plane onto which the detector elements and the base functions can be projected, whereas, if the detector elements and the base functions are not found in this plane, they must be projected into this plane.

LIST OF REFERENCE SIGNS $\alpha_{max}$ Beam angle of the beam
$\lambda_n$ Proportionality factor
$b_i(x)$ Spherical symmetrical base function
$c_i$ Image value of an image segment
$c_i^n$ Image value of the $i^{th}$ image segment after the $n^{th}$ iteration
$\tilde{p}_j$ Fictitious intermediate measured value
$p_j$ Measured value
T1 ... T17 Sub-areas of the detector area
$w_{ji}$ Proportionality factor
$x_i$ Grid points
x Position in object
f(x) Object image value at point x
S Source of beams
1 Gantry
2, 5 Motor
3 Collimator arrangement
4 Beam
7 Control unit
10 Reconstruction computer
11 Monitor
13 Area of examination
14 Axis of rotation
16 Detector unit
17 Helix-shaped trajectory
18 Detector area
22 Coordinate system
51 Area of a detector element
53 Projection center

The invention claimed is:

1. An imaging method, comprising the following steps:
generating rays penetrating an object in different directions by means of a radiation source;
acquisition of measured values, which depend on the intensity of the rays after penetration of the object, with a detector unit, which has a detector area divided into detector elements, wherein each detector element records a measured value; and
reconstruction of an object image by back projection of back projection values that depend on measured values;
wherein, the object image is divided into overlapping, quasi-spherically symmetric image segments, each one of which is defined by an image value and a quasi-spherically symmetric base function, the back projection values are added in proportions to the image values during the back projection, and the proportion of a back projection value, which is added to an image value during the back projection, is dependent on a proportionality factor, which is equal to the average value of the line integrals of the base function belonging to the respective image value along those rays that have generated the measured value on which the respective back projection value is dependent.

2. The imaging method as claimed in claim 1, wherein the proportion of a back projection value, which is added during the back projection to an image value is proportional to the respective proportionality factor.

3. The imaging method as claimed in claim 1, wherein each detector element has a rectangular area and that the proportionality factor for a hack projection value and an image value is determined with the following steps:
providing a table, in which each combination of radiation source position, detector element and image segment is assigned one or more sub-areas and average area values assigned to these sub-areas, wherein, each sub-area is rectangular and arranged in such a way that a corner of the respective sub-area coincides with a center of the base function of the image segment, which center is projected on the detector area along rays emanating from the radiation source position that is assigned to the respective sub-area, and that a diagonally opposite corner of the respective sub-area coincides with a corner of the rectangular area of the detector element to which the respective sub-area is assigned, and the average area value assigned to a sub-area is equal to the average value of the line integrals of the base function of the image segment, to which the respective sub-area is assigned, along those rays that strike the respective sub-area;
extracting those sub-areas and average area values from the table, which are assigned to that combination of radiation source position, detector element and image segment with which the radiation source position and the detector element determine the measured value on which the back projection value is dependent, for which the proportionality factor is to be determined, and with which the image segment has the image value, for which the proportionality factor is to be determined; and
adding and/or subtracting the extracted sub-areas, so that the area of the detector element results with which the measured value has been taken up, on which the back projection value is dependent, and adding and/or subtracting the associated, extracted average area values in the same direction, while the result of the addition and/or subtraction in the same direction is the proportionality factor.

4. The imaging method as claimed in claim 1, wherein several iterations are executed for the reconstruction of the object image, until an abort criterion is satisfied, wherein, initially the image values are set to an initial value and wherein new image values are determined in an iteration with the following steps:
forward projection along the generated rays through the object image, so that for each measured value a fictitious intermediate measured value is produced from image values;
determining differences between the fictitious intermediate measured values and the measured values as back projection values; and
back projection of the differences along the rays, wherein a proportion of a difference is added to each image value and wherein this proportion is dependent on the proportionality factor.

5. The imaging method as claimed in claim 4, wherein the proportion of a difference which is added to an image value, is proportional to the respective proportionality factor.

6. The imaging method as claimed in claim 4, wherein the initial value of the image values is equal to zero.

7. The imaging method as claimed in claim 1, wherein a computer having a computer memory that stores instructions that when executed on the computer, cause the computer to operate a control unit for controlling a radiation source, a detector unit, a driving arrangement and a reconstruction unit of a computer tomograph in accordance with the steps of the method.

8. The imaging method as claimed in claim 1, wherein the proportionality factor is determined by projecting the base function belonging to the respective image value onto the detector area and calculating the average value of the projection from an area of the detector element belonging to the respective image value.

9. The imaging method as claimed in claim 1, wherein the proportion of a back projection value, which is added during the back projection to an image value is proportional to the respective proportionality factor.

10. A computer tomograph for executing an imaging method comprising:
   a radiation source for generating an object-penetrating beam;
   a detector unit coupled to the radiation source;
   a driving arrangement to cause the object and the radiation source to rotate relatively to each other around an axis of rotation and/or to be movable parallel to the axis of rotation;
   a reconstruction unit for reconstructing the spatial distribution of the absorption of the object from the measured values acquired from the detector unit; and
   a control unit for controlling the radiation source, the detector unit, the driving arrangement and the reconstruction unit in accordance with steps of the imaging method, the steps comprising:
   generating rays penetrating the object in different directions by means of the radiation source;
   acquisition of measured values, which depend on the intensity of the rays after penetration of the object, with a detector unit, which has a detector area divided into detector elements, wherein each detector element records a measured value; and
   reconstruction of an object image by back projection of back projection values that de end on measured values;
   wherein, the object image is divided into overlapping, quasi-spherically symmetric image segments, each one of which is defined by an image value and a quasi-spherically symmetric base function, the back projection values are added in proportions to the image values during the back projection, and the proportion of a back projection value, which is added to an image value during the back projection, is dependent on a proportionality factor, which is equal to the average value of the line integrals of the base function belonging to the respective image value along those rays that have generated the measured value on which the respective back projection value is dependent.

11. The computer tomograph as claimed in claim 10, including a computer having a computer memory that stores instructions that when executed on the computer, cause the computer to operate the control unit for controlling the radiation source, the detector unit, the driving arrangement and the reconstruction unit of the computer tomograph in accordance with the steps of the imaging method.

12. The computer tomograph as claimed in claim 10, wherein each detector element has a rectangular area and that the proportionality factor for a back projection value and an image value is determined with the following steps:
   providing a table, in which each combination of radiation source position, detector element and image segment is assigned one or more sub-areas and average area values assigned to these sub-areas, wherein each sub-area is rectangular and arranged in such a way that a corner of the respective sub-area coincides with a center of the base function of the image segment, which center is projected on the detector area along rays emanating from the radiation source position that is assigned to the respective sub-area, and that a diagonally opposite corner of the respective sub-area coincides with a corner of the rectangular area of the detector element to which the respective sub-area is assigned, and the average area value assigned to a sub-area is equal to the average value of the line integrals of the base function of the image segment, to which the respective sub-area is assigned, along those rays that strike the respective sub-area;
   extracting those sub-areas and average area values from the table, which are assigned to that combination of radiation source position, detector element and image segment with which the radiation source position and the detector element determine the measured value on which the hack projection value is dependent, for which the proportionality factor is to be determined, and with which the image segment has the image value, for which the proportionality factor is to be determined; and
   adding and/or subtracting the extracted sub-areas, so that the area of the detector element results with which the measured value has been taken up, on which the back projection value is dependent, and adding and/or subtracting the associated, extracted average area values in the same direction, while the result of the addition and/or subtraction in the same direction is the proportionality factor.

13. The computer tomograph as claimed in claim 10, wherein several iterations are executed for the reconstruction of the object image, until an abort criterion is satisfied, wherein, initially the image values are set to an initial value and wherein new image values are determined in an iteration with the following steps:
   forward projection along the generated rays through the object image, so that for each measured value a fictitious intermediate measured value is produced from image values;
   determining differences between the fictitious intermediate measured values and the measured values as back projection values; and
   back projection of the differences along the rays, wherein a proportion of a difference is added to each image value and wherein this proportion is dependent on the proportionality factor.

14. The computer tomograph as claimed in claim 13, wherein the initial value of the image values is equal to zero.

15. The computer tomograph as claimed in claim 10, wherein the proportionality factor is determined by projecting the base function belonging to the respective image value onto the detector area and calculating the average value of the projection from an area of the detector element belonging to the respective image value.

* * * * *